United States Patent [19]

Amann et al.

[11] 4,011,336

[45] Mar. 8, 1977

[54] 3-(p-BIPHENYLYL)-BUTYRONITRILE AND THERAPEUTIC COMPOSITIONS CONTAINING THE SAME

[75] Inventors: August Amann, Ludwigshafen; Heinz Georg Vilhuber, Speyer; Johannes Kunze, Carlsberg; Hubert Giertz, Limburgerhof; Albrecht Franke, Ludwigshafen, all of Germany

[73] Assignee: BASF Aktiengesellschaft, Ludwigshafen (Rhine), Germany

[22] Filed: Nov. 28, 1975

[21] Appl. No.: 636,167

[30] Foreign Application Priority Data

Dec. 3, 1974 Germany .......................... 2456958

[52] U.S. Cl. ........................ 424/304; 260/465 R; 260/465 K; 260/515 R; 260/558 R
[51] Int. Cl.² ............ A61K 31/275; C07C 121/66
[58] Field of Search ................. 260/465 R; 424/304

[56] References Cited

OTHER PUBLICATIONS

Cavallini et al., Chemical Abstracts, vol. 51, 15461–15462 (1957).
Carissimi et al., Chemical Abstracts, vol. 59, 7518–7519 (1963).
"The Chemistry of Acrylonitrile," Second Edition, Cyanamid, p. 14, New York (1959).

*Primary Examiner*—Lewis Gotts
*Assistant Examiner*—Dolph H. Torrence
*Attorney, Agent, or Firm*—Johnston, Keil, Thompson & Shurtleff

[57] ABSTRACT 3-(p-Biphenylyl)-butyronitrile, its production and its use as an antiphlogistic agent.

4 Claims, No Drawings

3-(P-BIPHENYLYL)-BUTYRONITRILE AND THERAPEUTIC COMPOSITIONS CONTAINING THE SAME

The present invention relates to 3-(p-biphenylyl)-butyronitrile of the following formula

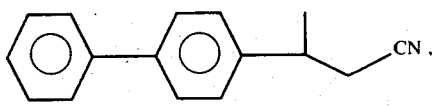

processes for its manufacture and a pharmaceutical comprising the same. The aforesaid compound can be used as a pharmaceutical, in particular as an antiphlogistic agent.

Antiphlogistic properties are known in the context of substituted arylalkanecarboxylic acids, in particular in respect of α-methylphenylacetic acids substituted in the phenyl group, and have been described, for example, by T. Y. Shen in Angew. Chem., Volume 84, pages 512 et seq. (1972). However, their effect if not always satisfactory. The therapeutic use of these acids is frequently limited by undesirable side effects.

It is apparent from the literature that in cases where antiphlogistic action is described in the context of derivatives of acids, such as esters, amides, substituted amines or hydroxamic acids (G. Lamberlin et al, Arzneimittelforschung 18, 1404 (1968), J. Wada et al., J. Med. Chem. 16, 930 (1973); M. Vincent et al., J. Med. Chem. 15, 75 (1972)) and the aldehyde and alcohols corresponding to such acids (Fried. et al. J. Med. Chem. 13, 203 (1970), the action of the corresponding acid is usually not attained by these derivatives. The corresponding acid nitriles have only been investigated in a few instances, for example by D. I. Barron et al. J. Med. Chem. 11, 1139 (1968), and their antiphlogistic action was clearly below the action of the acids or their derivatives.

It has now been discovered, surprisingly, that 3-(p-biphenylyl)butyronitrile is a highly active antiphlogistic agent.

The compound in accordance with the invention can be manufactured by catalytic hydrogenation of β-methyl-p-phenylcinnamic acid nitrile.

As a rule, the hydrogenation is carried out with hydrogen in a solvent, such as a lower alcohol, e.g. ethyl alcohol, an ether, e.g. tetrahydrofuran, glacial acetic acid or mixtures thereof, preferably in a mixture of equal proportions of ethyl alcohol and tetrahydrofuran in the presence of palladium on a carrier such as carbon or Raney nickel as a catalyst. The hydrogenation is carried out at atmospheric pressure or, if desired, at slightly increased pressure, and at temperatures between 25° and 50° C, preferably at room temperature.

An alternative method is to react a 2-(p-biphenylyl)-propyl halide, preferably the bromide or chloride, with an alkali metal cyanide such as sodium or potassium cyanide in a solvent such as ethanol, 2-methoxyethanol, dimethylformamide, dimethylsulfoxide or acetonitrile, preferably dimethylsulfoxide, at elevated temperatures, preferably from 80°– 160° C and more preferably between 80° and 100° C.

A further method involves, for example, the dehydration of 3-(p-biphenylyl)-3-methylpropionic acid amide with dehydrating agents such as phosphorus pentoxide, phosphorus oxychloride, phosphorus pentachloride, thionyl chloride, phosgene or aluminum chloride, or the dehydration of the ammonium salt of 3-(p-biphenylyl)-butyric acid with phosphorus pentoxide or glycerol.

The compound in accordance with the invention is distinguished by its good antiphlogistic action combined with very low toxicity and a broad therapeutic spectrum.

As compared with the corresponding 3-(p-biphenylyl)-butyric acid, which has also been proposed as an antiphlogistic agent, its toxicity is substantially lower, so that it has a considerably larger therapeutic spectrum.

The pronounced antiphlogistic action can be demonstrated in animal tests using rats with reference to the carrageenan paw edema. Female Sprague-Dawley rats weighing 105 to 140 g are used as test animals. 3-(p-Biphenylyl)-butyronitrile is administered orally in an amount of 20 ml/kg, in the form of 0.5% aqueous traganth suspension, 1 hour prior to the adminstration of carrageenan. 0.1 ml of a 1% carrageenan solution are in each case injected sub-plantar into the right hind paw. The volume of the paw is determined plethysmometrically 3½ hours after the administration of carrageenan and the volume increase in relation to the left untreated hind paw is calculated. The percentage reduction of the carrageenan paw edema as compared with animals which have not been pretreated serves as a measure of the antiphlogistic action of the test substance.

There exists a linear regression between the logarithmic values of the administered doses of the compound in accordance with the invention and the edema inhibition expressed as a percentage from which the parameter ED 33 [%] can be determined, being the dose for attaining a 33% inhibition of the carrageenan edema. For the substance in accordance with the invention (determined with 220 animals) it is 4.4 mg/kg. The ED 33 [%] of the known commercially available antiphlogistic agent phenylbutazone, used in the same test as a reference substance, is 7.9 mg/kg (determined with 80 animals). Accordingly, 3-(p-biphenylyl)-butyronitrile is 80% more effective than phenylbutazone.

The antiphlogistic action of the compound in accordance with the invention can also be demonstrated curatively with reference to established adjuvant arthritis in rats (male Sprague-Dawley rats, 200 to 250 g). The 3-(p-biphenylyl)-butyronitrile is administered orally once a day in 0.5% aqueous carboxymethylcellulose suspension in an amount of 10 ml/kg body weight. The animals are sacrificed after 11 days and the paw volumes (joint diameters) are determined.

| Antiphlogistic action in respect of adjuvant arthritis in rats | | |
|---|---|---|
| Substance | Dose [mg/kg] | Arthritis inhibition [%] ± $s_{\bar{x}}$ |
| 3-(p-biphenylyl)-butyronitrile | 2.15 | 72.4 ± 22.7 |
| Phenylbutazone | 17.8 | 74.5 ± 13.4 |

It appears from the table that according to this test 3-(p-biphenylyl)-butyronitrile is 8.3 times more effective than phenylbutazone.

The acute toxicity (24-hour value) is determined with male mice (NMRI, 18 to 24 g) by oral administration. The $LD_{50}$ for phenylbutazone determined with 140 animals is 853 (781 to 924) mg/kg. Even after the administration of the very high dose of 4640 mg/kg of 3-(p-biphenylyl)-butyronitrile there was no fatality amongst the 10 treated animals.

This demonstrates that the toxicity of the substance in accordance with the invention is exceptionally low. If, in addition to the toxicity, the almost double effectiveness of the substance as apparent from the carrageenan tests is taken into account, there is found a 10 times larger therapeutic spectrum as compared with phenylbutazone. An even more favorable relationship is found when comparing the toxicity and the effectiveness with reference to adjuvant arthritis. In that case 3-(p-biphenylyl)-butyronitrile has a therapeutic spectrum at least 45 times larger than that of phenylbutazone.

Accordingly, the invention also relates to a pharmaceutical composition characterized by a content of 3-(p-biphenylyl)-butyronitrile as an active ingredient besides conventional carriers or excipients.

Such pharmaceutical compositions comprising conventional carriers or excipients and the conventionally used pharmaceutical adjuvants may be manufactured in known manner appropriate to the desired route of administration and in dosage units appropriate for such administration.

A preferred pharmaceutical composition is provided in a form suitable for oral administration. Such forms include in particular tablets, coated tablets, dragees, capsules and, if desired, compositions which contain the active ingredient in solution. Suppositories may also be suitable.

The pharmaceutical compositions are appropriately in the form of dosage units corresponding to 20 to 250 mg, preferably 80 to 150 mg per dosage unit. The dose administered depends on the nature and severity of the condition. Daily doses of up to 2 g may be advantageous for therapeutic purposes.

Generally speaking, the compositions comprise the active ingredient to be used in accordance with the invention in combination with a carrier or diluted, together with a carrier or enclosed or encapsulated in a carrier in the form of a capsule, a sachet, a soluble capsule or another container serving as carrier and serving as a medium for administration, as a flavoring agent or as a diluent for the therapeutically active ingredient. Such carrier may be solid, a semi-solid or a liquid substance.

Suitable carriers are, for example, lactose, dextrose, sucrose, sorbitol, mannitol, starch, gum acacia, calcium phosphate, coconut butter, cocoa butter, alginates, tragacanth, methylcellulose and polyvinylpyrrolidone. A lubricant may be used for manufacturing tablets in order to prevent sticking or adhesion of the powdered components in the tableting molds or dies. Suitable lubricants are, for example, talcum and aluminum, magnesium or calcium stearate.

EXAMPLE 1

3-(p-Biphenylyl)-butylronitrile a. β-methyl-p-phenylcinnamic acid nitrile.

30 g (0.15 mole) of 4-phenylacetophenone are dissolved in 200 ml dimethylformamide. A mixture of 36 g (0.2 mole) diethylcyanomethylphosphonate and 32.5 g 30% sodium methylate solution (0.2 mole) in 50 ml dimethylformamide are added thereto dropwise with stirring in the course of 1 hour. The reaction solution is maintained for a further 3 to 4 hours at 40° C and is subsequently poured onto 1.5 l of ice water, the precipitate formed being suction filtered and washed with water. After recrystallization from ethanol there are obtained 27 g (80.6%) having a melting point of 138° to 139° C.

b. 3-(p-biphenylyl)-butyronitrile 25 g β-methyl-p-phenylcinnamic acid nitrile are dissolved in a mixture composed of 150 ml ethyl alcohol and 150 ml tetrahydrofuran and are hydrogenated in the presence of 1.5 g palladium on charcoal at 30° to 40° C and atmospheric pressure. After no more hydrogen is absorbed, the catalyst is filtered off, the solvent is distilled off and the residue is recrystallized from methanol. 20.3 g (80.5% yield) of 3-(p-biphenylyl)-butyronitrile are obtained having a melting point of 76° to 77° C.

EXAMPLE 2

27.5 g 2-(p-biphenylyl)-1-bromopropane are heated under reflux for 24 hours jointly with 7.4 g finely powdered sodium cyanide in 300 ml 90% ethyl alcohol. The reaction mixture is allowed to cool and the alcohol is distilled off under reduced pressure. The resulting residue is mixed with 500 ml water and extracted 3 times, each time with 100 ml of ether; the ether phase is separated off each time, dried, and evaporated down, whereafter the residue, after the addition of animal charcoal, is recrystallized from methanol.

16.7 g β-(p-biphenylyl)-butyronitrile (75.5% yield) of melting point 77° to 78° C are obtained, complying analytically with the formula $C_{16}H_{15}N$ (molecular weight 221.3), calculated C 86.84%, H 6.83%, N 6.33%; found: C 86.7%, H 6.7%. N 6.4%.

EXAMPLE 3

3 g dry finely powdered sodium cyanide are introduced into 50 ml absolute dimethylsulfoxide and briefly heated to 90° C on the water bath. The mixture is cooled to approximately 50° C and 11.5 g 2-(p-biphenylyl)-1-chloropropane dissolved in 10 ml dimethylsulfoxide are added dropwise in the course of 10 to 15 minutes in such a manner that the temperature during such addition does not rise above 150° to 160° C. Stirring is then continued until the temperature has dropped again to 50° C. The reaction mixture is poured onto approximately 300 ml water, followed by extraction with ether and recrystallization as described in Example 2 above.

9.6 g (83.5% yield) of β-(p-biphenylyl)-butyronitrile of melting point 77° to 78° C are obtained.

The 2-(p-biphenylyl)-1-halogen-propanes required as starting materials may be prepared by conventional methods from 2-(p-biphenylyl)-propanol-1 by reaction with, e.g., thionyl chloride, phosphorus trichloride, phosphorus pentachloride or phosphorus tribromide.

2-(p-biphenylyl)-1-bromopropane:

33.9 g 2-(p-biphenylyl)-propanol-1 and 7 ml pyridine are dissolved in 400 ml ether, cooled to −5° to +5° C, and 7 ml phosphorus tribromide dissolved in 100 ml ether are added dropwise in the course of 45 minutes. The reaction mixture is then agitated for 6 hours at room temperature, poured onto approximately 1.5 l of ice water and extracted with ether. The ether phase is washed several times with ice water, dried over sodium sulfate and potassium carbonate, filtered and evaporated down. The resulting residue (29.7 g crude product) is employed without further purification in the reaction according to Example 4.

2-p-Biphenylyl-1-chloropropane is obtained by reaction with phosphorus trichloride under analogous conditions.

2-(p-biphenylyl)-propanol-1:

3.25 g lithium aluminum hydride are suspended in 250 ml of absolute tetrahydrofuran. 22.6 g α-(p-biphenylyl)-propionic acid in 50 ml absolute tetrahydrofuran are then added dropwise at 10° to 15° C in the course of 2½ hours. The reaction solution is agitated for a further 3 hours. The product is then carefully decomposed with approximately 1 liter ice water, the precipitate being dissolved with 2N sulfuric acid, followed by extraction with ether. The ether phase is dried and evaporated down. 15.9 g crude product are obtained which can be converted further without prior purification. The pure compound melts at 60° to 63° C.

| Tablet recipe | |
|---|---|
| 3-(p-biphenylyl)-butyronitrile | 100 mg |
| polyvinylpyrrolidone (average mol.wt. 25,000) | 20 mg |
| polyethyleneglycol (average mol.wt. 4,000) | 14 mg |
| hydroxypropylmethyl cellulose | 40 mg |
| talcum | 4 mg |
| magnesium stearate | 2 mg |
| | 180 mg |

The active ingredient is moistened with polyvinylpyrrolidone in the form of a 10% aqueous solution, passed through a screen having 1.0 mm apertures and dried at 50° C. The granules are mixed with polyethylene glycol, hydroxypropylmethyl cellulose, talcum and magnesium stearate and pressed into tablets of 180 mg each.

| Dragee recipe | |
|---|---|
| 3-(p-biphenylyl)-butyronitrile | 120 mg |
| lactose | 60 mg |
| maize starch | 30 mg |
| polyvinylpyrrolidone | 4 mg |
| magnesium stearate | 1 mg |
| | 225 mg |

The mixture of the active ingredient, lactose and maize starch is granulated with the aid of an 8% aqueous solution of the polyvinylpyrrolidone through a screen of 1.5 mm mesh size, dried at 50° C and once again passed through a 1.5-mm screen. The granules thus obtained are mixed with magnesium stearate and pressed into tablet cores. The cores thus obtained are coated in the conventional manner with a coating composed essentially of sugar and talcum.

We claim:

1. 3-(p-Biphenylyl)-butyronitrile.
2. A therapeutic composition comprising in addition to a suitable carrier, excipient or diluent, an effective amount of 3-(p-biphenylyl)-butyronitrile as an active ingredient.
3. A therapeutic composition as claimed in claim 2 containing the active ingredient in an amount of 20 to 250 mg per dosage unit.
4. A therapeutic composition as set forth in claim 2 wherein the active ingredient is present in an amount of 80 to 150 mg per dosage unit.

* * * * *